United States Patent [19]

Ebner et al.

[11] 4,141,352
[45] Feb. 27, 1979

[54] ORAL HYGIENE APPLIANCE

[75] Inventors: Albert Ebner, St. Georgen; Kurt Bäuerle, Schramberg, both of Fed. Rep. of Germany

[73] Assignee: Kuno Moser GmbH, Roggenbachweg, Fed. Rep. of Germany

[21] Appl. No.: 727,689

[22] Filed: Sep. 29, 1976

[30] Foreign Application Priority Data

Oct. 4, 1975 [DE] Fed. Rep. of Germany ....... 2544534

[51] Int. Cl.² .............................................. A61H 9/00
[52] U.S. Cl. .................................................. 128/62 A
[58] Field of Search ......................... 128/41, 62 A, 66; 417/410, 411, 415; 222/325, 542, 67; 310/29, 36, 37, 38

[56] References Cited

U.S. PATENT DOCUMENTS

| | | | |
|---|---|---|---|
| 1,995,424 | 3/1935 | Guinness | 128/62 A |
| 2,305,943 | 12/1942 | Weyandt | 310/29 |
| 3,075,471 | 1/1963 | Miller | 310/36 |
| 3,227,158 | 1/1966 | Mattingly | 128/62 A |
| 3,393,673 | 7/1968 | Mattingly | 128/62 A |
| 3,401,690 | 9/1968 | Martin | 128/62 A |
| 3,420,228 | 1/1969 | Kalbfeld | 128/62 A |
| 3,425,410 | 2/1969 | Cammack | 128/62 A |
| 3,493,793 | 2/1970 | Niemela | 310/37 |
| 3,800,786 | 4/1974 | Kovach | 128/62 A |
| 3,851,643 | 12/1974 | Musy | 128/62 A |
| 3,915,341 | 10/1975 | Brown | 222/67 |
| 4,022,174 | 5/1977 | Brinkman | 417/410 |

*Primary Examiner*—Robert W. Michell
*Assistant Examiner*—V. Millin
*Attorney, Agent, or Firm*—Peter K. Kontler

[57] ABSTRACT

An oral irrigating appliance wherein the pump which draws liquid from a reservoir and delivers spurts of liquid to a jet tip has a reciprocable piston which receives motion from one arm of an oscillatable two-armed armature forming part of a three-pole electromechanical oscillator connectable to a source of alternating current. The quantity of liquid which the pump delivers to the jet tip per unit of time is variable by changing the amplitude of oscillations of the armature. The pump receives liquid by way of an inlet valve whose valve element is opened by inflowing liquid when the piston performs a suction stroke, and the pump delivers liquid to the jet tip by way of an outlet valve having a valve element which is opened by liquid when the piston performs a compression stroke. The valve element of the inlet valve is closed by liquid when the piston performs a compression stroke, and the valve element of the outlet valve is closed, with a preselected delay, when the piston performs a suction stroke.

37 Claims, 10 Drawing Figures

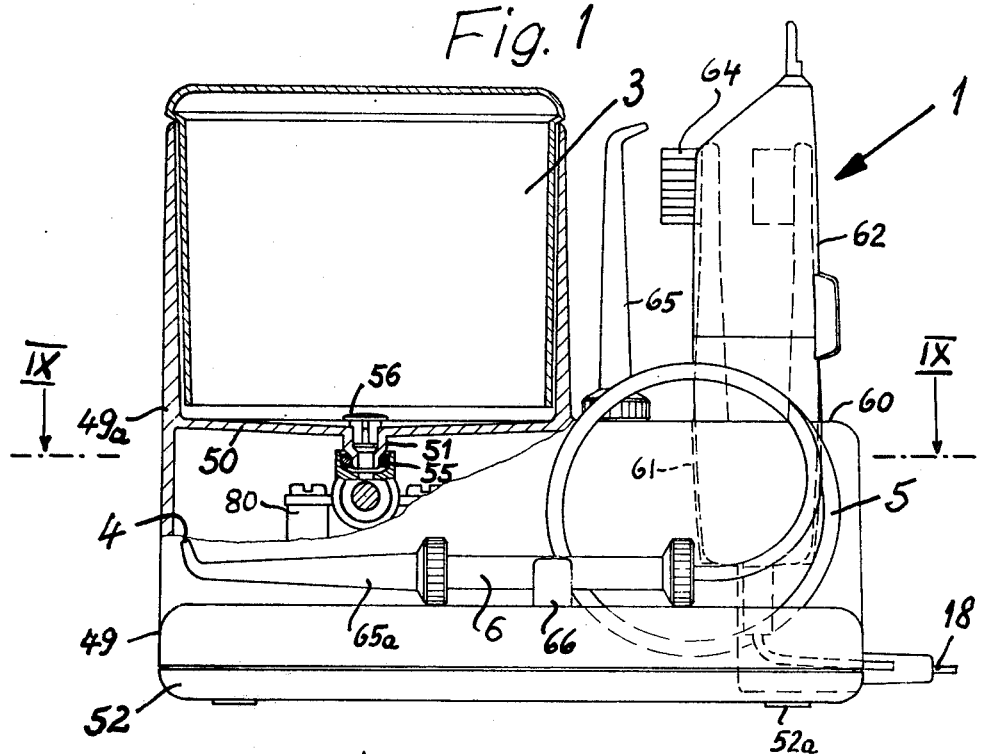
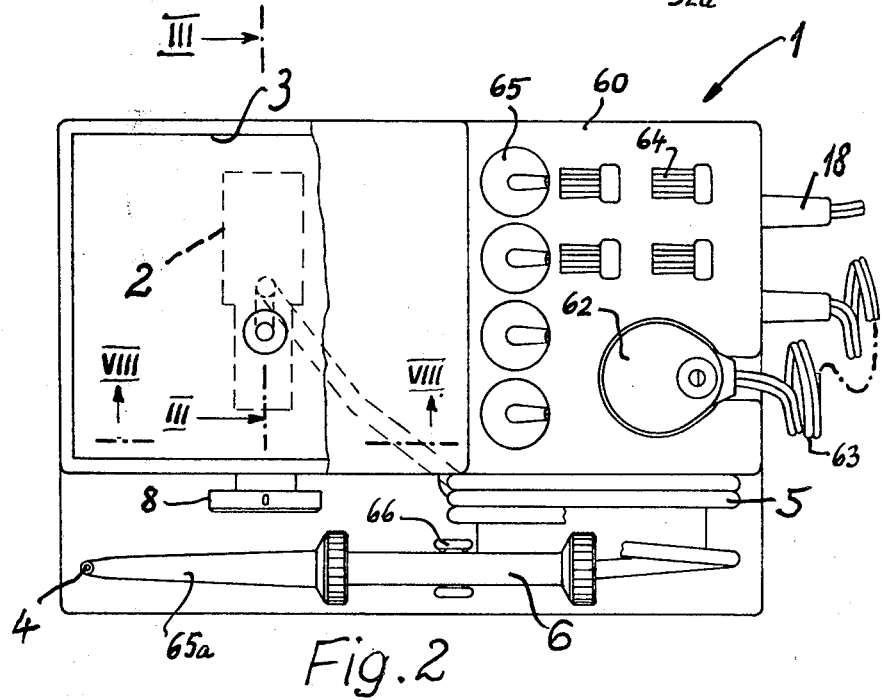

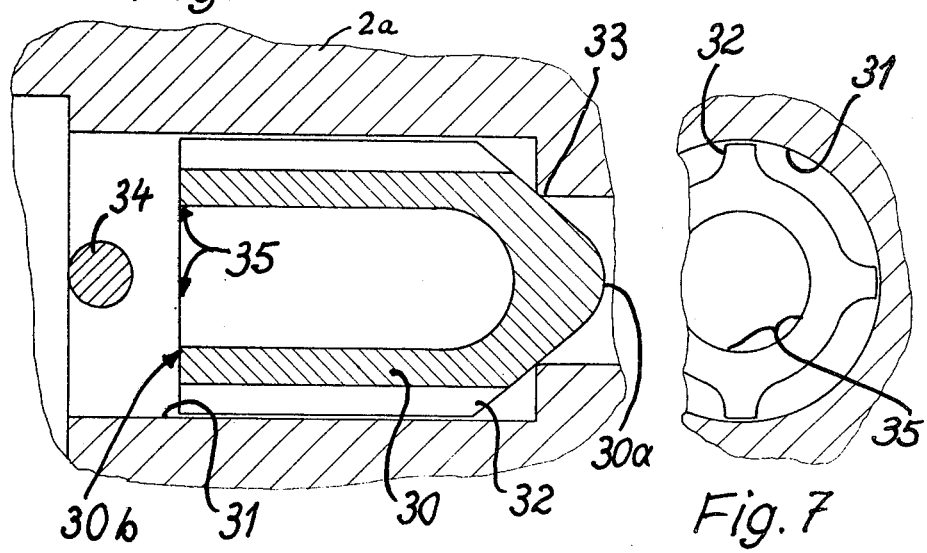
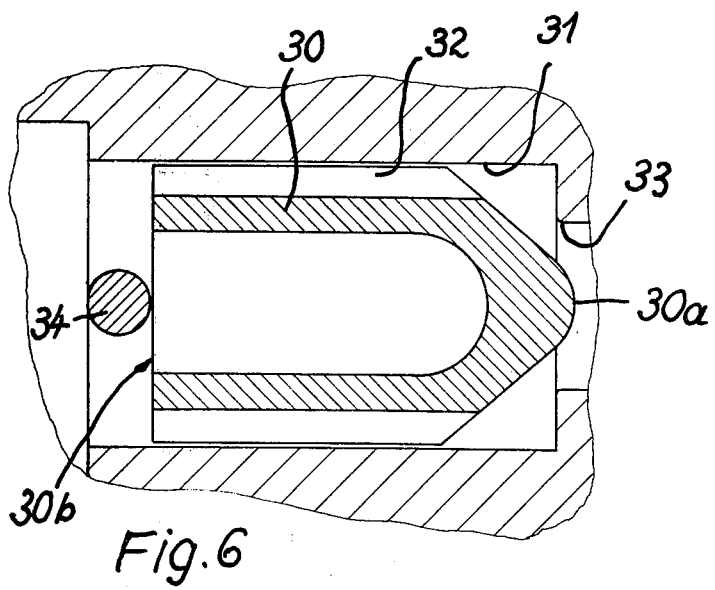

ORAL HYGIENE APPLIANCE

BACKGROUND OF THE INVENTION

The present invention relates to oral hygiene appliances in general, and more particularly to improvements in so-called oral irrigating appliances. Still more particularly, the invention relates to improvements in oral hygiene appliances of the type wherein spurts or surges of water or a water-containing liquid are used for the cleaning of teeth, bridgework, crowns and orthodontic appliances as well as for invigorating the gums. In such appliances, spurts of water are produced by a motor-driven pump, e.g., a peristaltic pump or a pump utilizing a reciprocating piston.

In conventional oral hygiene appliances, the pressure of liquid which issues from the orifice of the nozzle (called jet tip) is regulated by way of the pump. In many instances, the pressure outlet of the pump is connected with the inlet by a conduit which contains suitable means for regulating the quantity of liquid that flows from the outlet back to the inlet. Such pressure regulating means are complex, prone to malfunction and rather expensive. Moreover, and if the pump comprises a reciprocating piston which receives motion from the rotary output element of an electric motor, the means (e.g., a crank drive) which converts rotary motion of the output element into reciprocatory motion of the piston is bulky, complex and expensive, especially since the dimensions of the pump and motor in an oral hygiene appliance are normally extremely small. Furthermore, presently known appliances are quite noisy and their useful life is relatively short.

SUMMARY OF THE INVENTION

An object of the invention is to provide an oral hygiene appliance which is simpler, more rugged, more compact and less expensive than heretofore known appliances, which generates less noise than a conventional appliance, and wherein the intensity of spurts of liquid which issue from the orifice of the nozzle can be regulated in a novel and improved way.

Another object of the invention is to provide a novel and improved prime mover for the pump of an oral hygiene appliance.

A further object of the invention is to provide novel and improved valves which permit the flow of liquid to and from the pump of the above-outlined appliance.

An additional object of the invention is to provide a novel and improved motion transmitting connection between the prime mover and the pump of an oral hygiene appliance.

An ancillary object of the invention is to provide a novel and improved separable connection between the liquid reservoir and the pump of the above-outlined appliance.

A further object of the invention is to provide an oral hygiene appliance wherein the reservoir is automatically sealed from the pump when the prime mover for the pump is arrested.

Another object of the invention is to provide an oral irrigating appliance which can discharge spurts of cold, tepid or hot liquid even if the reservoir contains a supply of cold liquid.

An additional object of the invention is to provide an appliance which is compact enough to be readily stored in a briefcase, which can carry a requisite supply of spare jet tips and/or other implements for cleaning and other care of teeth and/or gums, and whose controls are simpler than those of conventional appliances.

A further object of the invention is to provide the appliance with novel and improved means for changing several characteristics of the spurts of liquid prior to starting of the prime mover or while the prime mover is on.

One feature of the invention resides in the provision of an oral hygiene appliance of the type known as oral irrigating apparatus or oral irrigator. The appliance comprises a liquid reservoir, a nozzle (also called jet tip), a pump having means (preferably a piston or an analogous reciprocating pumping element) for drawing liquid from the reservoir (whenever the piston performs a suction stroke) and for delivering spurts of liquid to the nozzle (whenever the piston performs a compression stroke), and prime mover means for driving the pump. The prime mover means comprises a multi-pole electromechanical oscillator (preferably an oscillator having three poles) with an oscillatory armature and with means (e.g., a cable) for connecting the poles of the oscillator to a source of alternating current (e.g., 50-cycle alternating current). The means for transmitting motion from the armature to the piston preferably comprises two pin-shaped connecting or coupling elements one of which is secured to the armature and the other of which is coupled to the one coupling element and is disposed substantially diametrically of and can reciprocate in the piston.

The quantity of liquid which is discharged into the nozzle per unit of time can be regulated by changing the amplitude of oscillations of the armature, i.e., by changing the length of strokes of the piston in the body of the pump.

The novel features which are considered as characteristic of the invention are set forth in particular in the appended claims. The improved appliance itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a schematic front elevational view of an oral hygiene appliance which embodies the invention, with certain components partly broken away or shown in vertical section;

FIG. 2 is a plan view of the appliance, with a portion of the cover for the reservoir broken away;

FIG. 5 is a greatly enlarged axial sectional view of one of two valves which control the flow of liquid to and from the pump, the valve element being shown in closed or sealing position;

FIG. 6 shows the structure of FIG. 5 but with the valve element in open position;

FIG. 7 is an end elevational view as seen from the left-hand side of FIG. 5;

DESCRIPTION OF THE PREFERRED EMBODIMENTS

Figure 3:
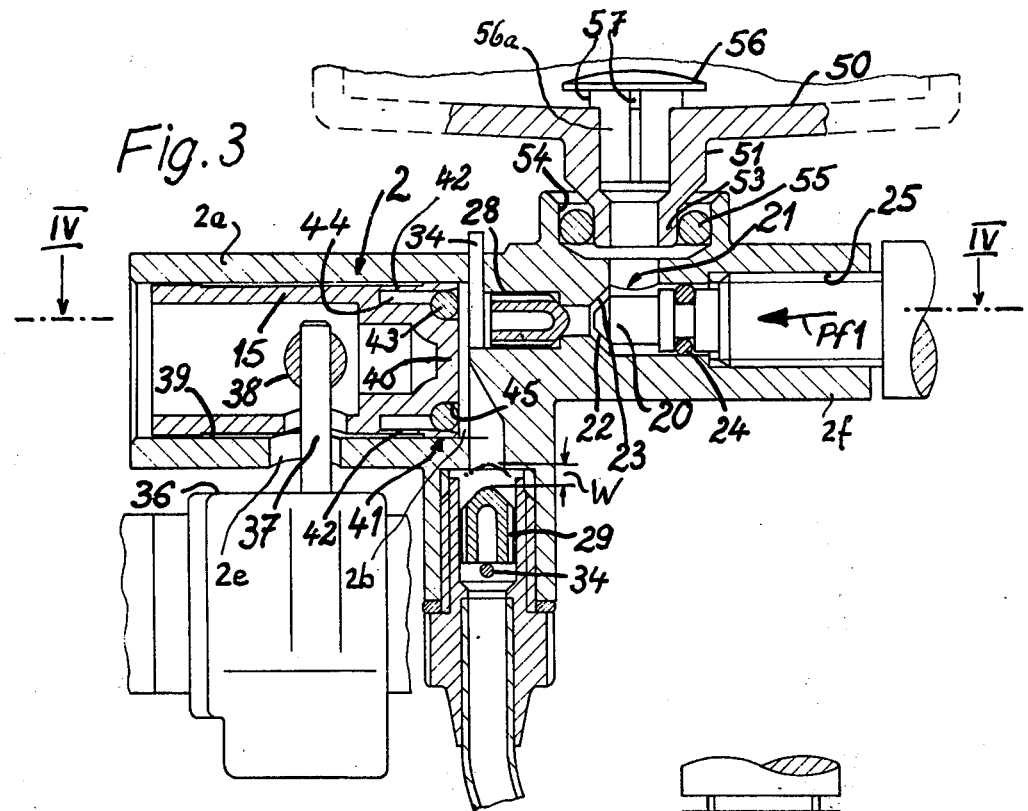
FIG. 3 is an enlarged fragmentary vertical sectional view, substantially as seen in the direction of arrows from the line III—III of FIG. 2.

Referring first to FIGS. 1 and 2, there is shown an oral hygiene appliance which comprises a housing 1 including a base 52 with legs 52a and a platform 60 with a socket 61 for an electric toothbrush 62 having a separate cable 63 for connection to an energy source. The platform 60 has additional sockets for brushes 64 and a battery of spare jet tips or nozzles 65. The platform 60 forms part of a hollow housing section 49 which is separably mounted on the base 52 and carries a clamp 66 for the holder 6 of that jet tip (65a) which is ready for use. The holder 6 is a tube which is connected with the discharge end of a flexible conduit or hose 5 serving to supply spurts of liquid when a pump 2 (mounted in the interior of the housing section 49) is driven by a prime mover 7 (shown in FIGS. 4 and 9). The pump 2 draws liquid from a reservoir 49a which forms part of the housing section 49 and is adjacent to the platform 60. A removable cover 3 is inserted into the reservoir 49a when the appliance is not in use; this cover can be inserted into the reservoir as soon as the latter receives a supply of liquid (either water or a mixture of water with a concentrated tooth cleaning agent and/or breath freshener). The orifice of the jet tip 65a is shown at 4.

Figure 8:
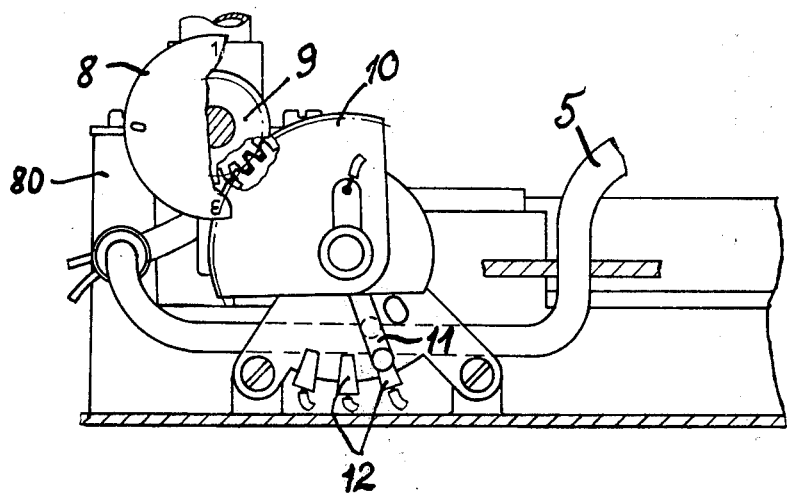
FIG. 8 is an enlarged fragmentary vertical sectional view, substantially as seen in the direction of arrows from the line VIII—VIII of FIG. 2 and showing the means for regulating the quantity of liquid which is discharged per unit of time.

The prime mover 7 is a three-pole electromechanical oscillator having an armature 14 which is pivotable on an upright pivot member of shaft 26 mounted in the housing 1. The armature 14 is biased to neutral position by two helical springs 19 which react against suitable retainers 19a of the housing section 49 or base 52. The amplitude of oscillations of the armature 14 can be regulated, either stepwise or infinitely, by a rotary actuating member or knob 8 shown in FIGS. 2, 8 and 9. The illustrated knob 8 is assumed to form part of means for stepwise regulation of the amplitude of armature 14. The regulating means further comprises a gear 9 which is coaxial with and receives motion from the knob 8, and a gear segment 10 which meshes with the gear 9 and carries a movable electric contact 11 which can engage a selected one of three stationary contacts 12 in the housing section 49. When the movable contact 11 engages the leftmost contact 12 of FIG. 8 or 9, the circuit of the prime mover 7 is completed by way of a conductor 12a whereby the amplitude of oscillations of the armature 14 is maintained at a maximum value. The amplitude is reduced when the movable contact 11 engages the median contact 12 because the circuit of the prime mover 7 is then completed by way of conductors 12b, 12c which are connected to each other by the right-hand resistor 13 of FIG. 9. The amplitude is reduced still further if the movable contact 11 engages the right-hand contact 12 because the circuit of the prime mover 7 is then completed by way of conductors 12d, 12c, i.e., by way of two resistors 13. The fixed contacts 12 and the resistors 13 determine the strength of current which is supplied to the energizable poles 7a, 7b, 7c of the prime mover 7 and hence the strength of magnetic fields which are produced by the poles to attract or repel the adjacent longer arm of the armature 14. The manner in which the poles 7a–7c and the springs 19 cooperate to oscillate the armature 14 when the circuit of the prime mover 7 is completed by the knob 8 is known and need not be described here.

Figure 9:
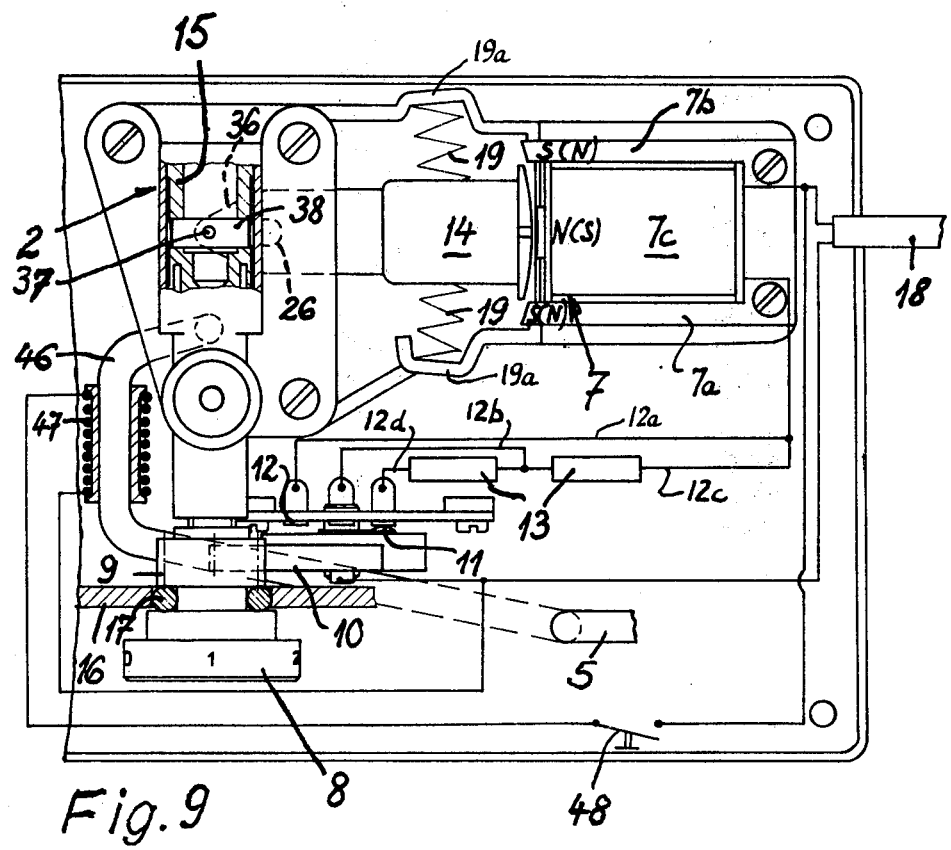
FIG. 9 is a fragmentary horizontal sectional view of the appliance, substantially as seen in the direction of arrows from the line IX—IX of FIG. 1.

The amplitude of the armature 14 determines the extent of reciprocatory movement of a pumping element or piston 15 which forms part of the pump 2 and is articulately connected with the shorter arm 36 of the armature. The extent of reciprocatory movement of the piston 15 determines the quantity of liquid which is discharged by the orifice 4 of the jet tip 65a per unit of time. The frequency of oscillation of the armature 14 is constant. The knob 8 is further movable to a neutral or zero position in which the circuit of the prime mover 7 is open because the movable contact 11 does not engage a stationary contact 12. As shown in FIG. 9, the shank of the knob 8 extends forwardly through the front wall 16 of the housing section 49 and is surrounded by a suitable sealing element 17, e.g., an O-ring.

Figure 10:
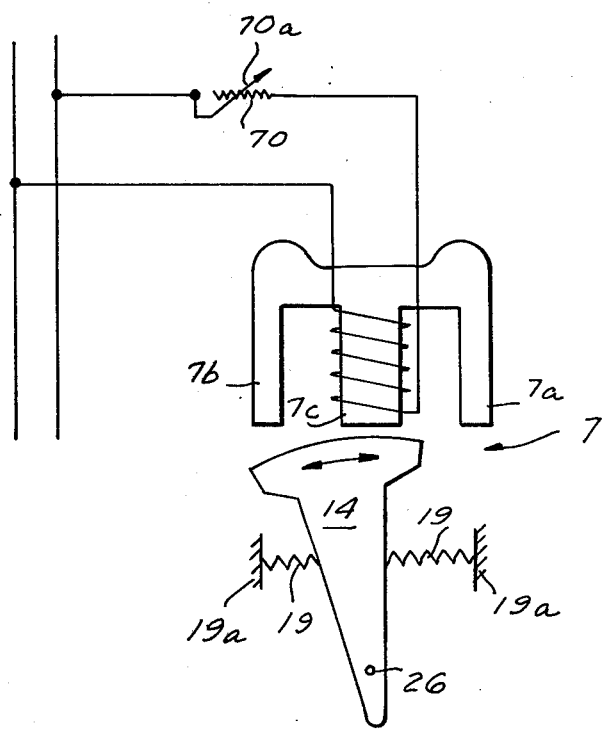
FIG. 10 is a fragmentary plan view of a modified prime mover for the pump.

If desired, the means for regulating the amplitude of the armature 14 may comprise a variable resistor 70 (shown in FIG. 10) whose slider 70a is attached to the knob in a manner not shown in FIG. 10 and which can select any one of an infinite number of amplitudes. The knob for the slider 70a of the regulating means shown in FIG. 10 is provided with an index which can move with respect to a suitably graduated scale at the outer side of the wall 16 to indicate the selected amplitude of the armature 14.

The prime mover 7 is connectable with a source of alternating current by means of a cable 18 having a plug, not shown, for insertion into a conventional household outlet. The frequency of the piston 15 equals the frequency of the armature 14.

The bias of the springs 19 for the armature 14 and the masses of moving parts (14, 15) are selected in such a way that the piston 15 is reciprocated at the desired frequency (e.g. 50 cycles per second). Thus, the adjustment may be such that the characteristic frequency of moving parts corresponds to the frequency of the prime mover 7. In each instance, the frequency of alternating current is a whole multiple (including one) of the frequency of piston 15 and armature 14.

An important advantage of the prime mover 7 over prime movers having rotary output elements is that the operative connection between the oscillatory armature (output element) 14 and the reciprocatory piston 15 is much simpler than the operative connection between a rotary output element and a reciprocable driven part. Moreover, the quantity of liquid which is discharged by the pump 2 per unit of time can be regulated by regulating the prime mover 7 rather than the pump. The regulation is very simple and inexpensive because the frequency of oscillations of the armature 14 remains constant, i.e., it is only necessary to change the amplitude of the armature and hence the length of strokes of the piston 15 in the body 2a of the pump 2. If the prime mover of the appliance were to constitute an electric motor with a rotary output element, regulation of the motor (i.e., changing the RPM of the output element and hence the quantity of liquid which a reciprocating piston displaces per unit of time) would invariably entail a change in the number of piston strokes per unit of time.

Furthermore, the operation of the pump (particularly the noise) is not affected by changing the amplitude of the armature 14. This is in contrast to operation of conventional oral irrigating appliances wherein the piston of the pump receives motion from a rotary output element through the medium of a crank drive; in such appliances, the noise level invariably increases in response to an increase of RPM of the output element.

Still further, regulation of the quantity of liquid which is expelled from the orifice 4 of the jet tip 65a per unit of time does not or need not involve any return flow of liquid from the outlet toward and into the inlet of the pump. This is desirable because the operation of the improved appliance is more economical, i.e., any liquid which has been sucked into the chamber 2b of the pump body 2a invariably flows toward and into the hose 5.

Finally, the cost of the improved prime mover 7 is but a fraction of the cost of a prime mover with a rotary output element and with a crank drive between such output element and the reciprocable component or components of the pump.

The knob 8 is operatively connected with and transmits torque to the valve element 20 of a shutoff valve which is installed in a passage 21 connecting the outlet of the reservoir 49a with the inlet of the pump 2 (see FIG. 3). When the knob 8 is moved to its neutral position (in which the circuit of the prime mover 7 is open because the movable contact 11 is disengaged from the stationary contacts 12), the conical tip 22 of the valve element 20 engages a conical seat 23 in the passage 21 and seals the chamber 2b of the pump 2 from the reservoir 49a. The knob 8 transmits torque to an externally threaded member or extension 25 which meshes with an internally threaded member or sleeve 2b of the pump body 2a. FIG. 3 shows the valve element 20 in open position, i.e., the knob 8 is assumed to dwell in an angular position in which the mobile contact 11 engages one of the stationary contacts 12. The direction in which the extension 25 moves in response to rotation of the knob 8 toward neutral position is indicated by the arrow Pf1. The valve element 20 has a smaller-diameter portion or neck which is surrounded by a sealing element 24 bearing against the adjacent internal surface of the pump body 2a to prevent leakage of liquid from the passage 21 along the periphery of the extension 25. The knob 8 need not move axially with the valve element 20; for example, the rear or inner end face of the shank of the knob 8 may be provided with a diameterically extending lug which is received in a complementary slot in the front end face of the extension 25. An important advantage of the shutoff valve including the element 20 is that this valve automatically prevents leakage of liquid by way of the orifice 4 of the jet tip 65a when the prime mover 7 is off, regardless of whether or not the reservoir 49a contains liquid at the time the prime mover is arrested by moving the knob 8 to its neutral position. Furthermore, the sealing action of the shutoff valve is independent of the positions of valve elements which form part of the inlet and outlet valves 28, 29 for the pump 2.

Figure 4:
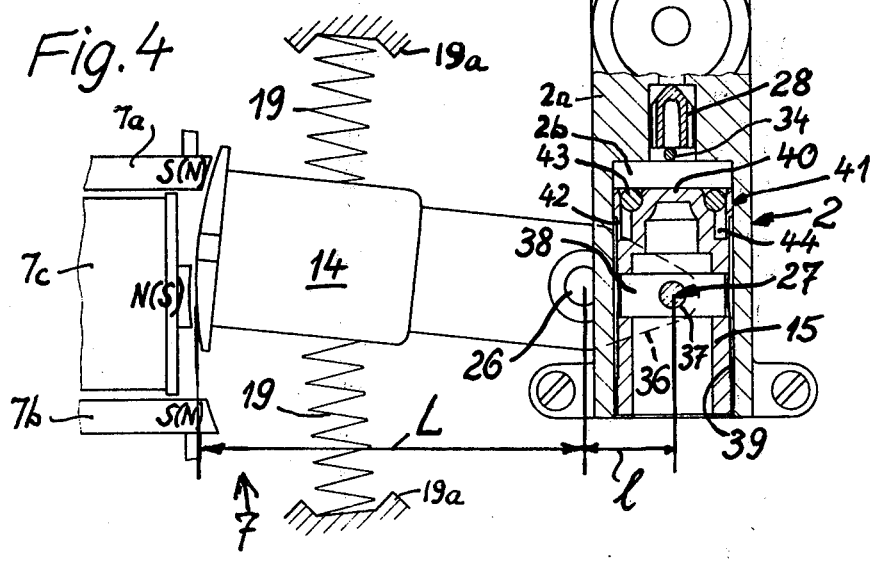
FIG. 4 is a smaller-scale sectional view, substantially as seen in the direction of arrows from the line IV—IV of FIG.3.

It has been found that the extent of reciprocatory movement of the piston 15 at each amplitude of the armature 14 is highly satisfactory if the ratio of the length L of longer arm to the effective length l of the shorter arm 36 of the armature 14 is approximately five to one, most preferably 4½ to one (see FIG. 4). The effective length of the shorter arm 36 is that between the axis of the shaft 26 for the armature 14 and the axis 27 of a connecting member or pin 37 which couples the arm 36 to the piston 15. The extent of reciprocatory movement of the piston 15 is proportional to the amplitude of the armature 14.

The appliance further comprises the aforementioned inlet and outlet valves 28, 29 for the pump 2. The inlet valve 28 has a reciprocable valve element 30 (see FIGS. 5 to 7) which is installed in a portion 31 of the passage 21 downstream of the valve element 20 of the shutoff valve. The outlet valve 29 comprises a similar reciprocable valve element which is installed between the chamber 2b and the inlet of the hose 5. The maximum stroke W of the valve element of the outlet valve 29 is selected in such a way that this valve element assumes its closing position (indicated in FIG. 3 by a dotted line) while the piston 15 already performs a suction stroke. This insures that the piston 15 draws some liquid from the body of the outlet valve 29 simultaneously with entry of liquid into the chamber 2b by way of the inlet valve 28. Such mode of operation contributes to more pronounced pulsation of the liquid which issues from the orifice 4 of the jet tip 65a. The stroke W can be readily selected in such a way that the quantities of liquid which flows from the hose 5 and back toward the chamber 2b are relatively small. The maximum stroke of the valve element 30 of the inlet valve 28 is preferably less (and most preferably substantially less) than the stroke W so that the quantity of liquid which is forced from the chamber 2b back toward the annular seat 23 for the valve element 30 while the piston 15 performs a compression stroke (to expel liquid from the chamber 2b into the hose 5) is negligible.

The construction of the inlet valve 28 is shown in detail in FIGS. 5 to 7. The valve element 30 is reciprocable in the portion 31 of the passage 21 and its peripheral surface is formed with several centering fins 32 slidable along the surface which surrounds the portion 31. The rounded conical end portion or tip 30a at that end of the valve element 30 which faces counter to the direction of liquid flow toward the chamber 2b abuts against the annular seat 33 of the body 2a when the inlet valve 28 is closed (see FIG. 5). The maximum stroke of the valve element 30 is determined by a stop 34 which is a pin mounted in the body 2a and extending diametrically of the valve element 30. The latter is hollow to reduce its inertia (see the blind bore 35 which is provided in the flat left-hand end face 30b of the element 30, i.e., in that end face which faces toward the chamber 2b). The inlet valve 28 need not be provided with a valve spring, i.e., the valve element 30 can move between the end positions of FIGS. 5 and 6 solely under the action of liquid which flows from the reservoir 49a toward the chamber 2b or from the chamber 2b toward and through the outlet valve 29. The tip 30a of the valve element 30 may but need not be conical; this tip may constitute a substantially hemispherical body. Alternatively, the tip 30a may constitute a pointed cone.

When the valve element 30 is held in the open position of FIG. 6, streamlets of liquid can flow from the seat 23 toward and through the seat 33 and thereupon through the channels between the fins 32 on their way into the chamber 2b of the pump body 2a. Such flow of liquid takes place when the piston 15 performs a suction stroke. When the piston 15 thereupon moves in a direction to expel liquid from the chamber 2b, the liquid applies pressure against the end face 30b as well as against the bottom surface of the bore 35 and moves the valve element 30 to the position of FIG. 5 in which the tip 30a sealingly engages the seat 33. The fins 32 terminate short of the locus where the tip 30a engages the seat 33 when the inlet valve 28 is closed; this insures that the valve element 30 can prevent any and all leakage of liquid when it assumes the position of FIG. 6.

The construction of the outlet valve 29 is preferably (but need not be) identical with that of the inlet valve 28. In the illustrated embodiment of the appliance, the only difference between the valves 28 and 29 is that the stroke W of the valve element in the outlet valve 29 is longer than that of the valve element 30 in the inlet valve 28. However, it is equally within the purview of the invention to provide a valve spring for the valve element 30 of the valve 28 and/or 29 even though the illustrated constructions are preferred because the appliance requires less maintenance and the valves 28 and 29 are less prone to malfunction. Since the mass of the valve elements 30 (these elements preferably consist of a lightweight synthetic plastic material) is negligible, the valve elements can readily reciprocate at the frequency of the armature 14 and/or piston 15. The resistance which the valve elements offer to movement in the direction of fluid flow through the respective valves 28, 29 is very small. On the other hand, these valve elements can furnish a highly satisfactory sealing action against the flow of liquid counter to the desired direction. An exception is the valve element of the outlet valve 29 which preferably allows some liquid to flow from the hose 5 back toward the chamber 2b during the initial stage of each suction stroke of the piston 15. However this is attributable to the relatively long stroke W of the valve element in the outlet valve 29.

FIG. 3 shows that the axis of the valve element in the outlet valve 29 is vertical or nearly vertical so that the valve element tends to move to its open position by gravity and must be lifted to closed position by the piston 15 when the latter performs the second stage of a suction stroke. Such mounting of the valve element in the outlet valve 29 is preferred at this time because it contributes to relatively slow movement of the valve element to the sealing or closed position. As mentioned above, delayed closing of the outlet valve 29 contributes to more pronounced pulsation of liquid which issues from the jet tip 65a by way of its orifice 4. The path of reciprocatory movement of the valve element 30 in the inlet valve 28 is preferably horizontal or nearly horizontal so that the influence of gravity on this valve element is nil or negligible.

The housings for the valve elements of the valves 28, 29 are defined by the respective portions of the pump body 2a.

The details of the operative motion transmitting connection between the shorter arm 36 of the armature 14 and the piston 15 of the pump 2 are shown in FIGS. 3 and 4. The arm 36 is located at one side of the piston 15 and carries the aforementioned connecting member or pin 37 which extends radially of the piston and into a complementary bore of the second connecting member of crosspin 38 which is reciprocable in a diametrically extending bore of the piston 15. The pin 37 can rotate relative to the crosspin 38 and the latter is reciprocable relative to the piston 15; this insures that the armature 14 can pivot about the axis of the shaft 26 and the piston 15 can reciprocate in the cylinder of the body 2a without any jamming. The pin 37 is preferably normal to the plane of the arm 36.

FIG. 4 shows the piston 15 in one of its end positions, namely in that end position which the piston assumes upon completion of a suction stroke. The volume of the chamber 2b in the pump body 2a has been increased to a maximum value and the valve element 30 of the inlet valve 28 abuts against the respective stop 34. The crosspin 38 is in the left-hand end position. When the piston 15 thereupon reaches its neutral position (midway between the two end positions), the crosspin 38 is located at a maximum distance from the shaft 26, and the crosspin 38 reassumes its left-hand end position when the piston 15 reaches the other end position in which the volume of the chamber 2b is reduced to a minimum. It has been found that the just discussed motion transmitting connection allows for reciprocatory and surprisingly quiet movement of the piston 15 along a straight path in spite of the fact that the axis 27 of the pin 37 swings back and forth about the axis of the shaft 26.

FIGS. 3 and 4 further illustrate the manner in which the piston 15 is designed in order to avoid leakage of fluid from the chamber 2b in a direction to the left, as viewed in FIG. 3. Such leakage must be avoided or kept to a minimum in spite of the relatively high frequency of reciprocatory movement of the piston 15. Moreover, the wear upon the piston 15 and/or the cylinder of the body 2a should be negligible and the friction between these parts should be minimal in order to reduce the energy requirements of the prime mover 7 and to insure long periods of useful life of the pump.

The major portion of the piston 15 is received in the bore 39 of the cylinder of the pump body 2a with a readily discernible clearance or play (see particularly FIG. 3). That end wall (40) of the piston 15 which is immediately adjacent to the chamber 2b has a relatively thin elastic annular portion or skirt 42 which bears against the surrounding portion 41 of the internal surface surrounding the bore 39 to establish a highly satisfactory seal which prevents the flow of liquid from the chamber 2b toward and into the aforementioned clearance around the major portion of the piston 15. The skirt 42 prevents leakage of liquid around the piston 15 in spite of the fact that the major portion of the piston is received in the bore 39 with a pronounced clearance. Since the skirt 42 is relatively short and is deformable (it can but need not be slotted), friction between the piston 15 and body 2a is negligible. Moreover, the elasticity of the skirt 42 compensates for eventual wear upon the abutting surfaces of the piston and pump body. The just described seal is simpler, longer-lasting, more reliable and less expensive than elastic piston rings or analogous conventional sealing elements between the periphery of a reciprocating piston and the internal surface of the associated cylinder. Moreover, the cost of the piston 15 is but a fraction of the cost of a piston with one or more rings.

The skirt 42 surrounds an annular groove 44 which is provided in the exposed end face of the bottom wall 40 of the piston 15, and the enlarged outermost portion 45 of the groove 44 receives an elastic sealing element 43 (e.g., an O-ring) which biases the skirt 42 against the adjacent portion 41 of the surface surrounding the bore 39. The ring 43 constitutes a means for spreading or expanding the skirt 42 against the adjacent internal surface of the body 2a. The provision of ring 43 simplifies the mounting of the piston 15 in the body 2a. The piston 15 preferably consists of a suitable synthetic plastic material and may be produced at a low cost and with a high degree of accuracy and reproducibility, by injection molding or by resorting to another conventional mass-producing technique. The outer diameter of the piston 15 may be between 6 and 20 millimeters, preferably about 12 millimeters. The major part of the piston 15 is preferably hollow (see FIG. 3) so that its mass is very small and the piston can be readily reciprocated at the frequency of the armature 14. The pin 37 on the arm 36 of the armature 14 extends through an elongated slot 2e of the body 2a and a radial bore in the hollow cylindrical portion of the piston 15 to the left of the skirt 42, as viewed in FIG. 3.

FIG. 9 shows that the section 49 of the housing 1 can contain an electric heating device 47 which is a coil surrounding the intake portion 46 of the hose 5. The circuit of the coil 47 can be completed by closing a switch 48 which is preferably accessible at the front side of the housing 1 adjacent to the knob 8. If desired, the circuit of the coil 47 can be completed in automatic response to movement of the knob 8 from its neutral position. The provision of a discrete operating means (switch 48) for the heating coil 47 is preferred at this time since the user might decide to fill the reservoir 49a with tepid or relatively hot water so that the heating of liquid which flows from the chamber 2b toward the orifice 4 of the jet tip 65a is unnecessary. It is also possible to provide the appliance with means for regulating the heating action of the coil 47 so that the user can select the temperature of spurts of liquid which issue from the orifice 4, even if the reservoir 49a is filled with or contains a supply of cold liquid.

The means for establishing communication between the passage 21 and the reservoir 49a is shown in FIGS. 1 and 3. The bottom wall 50 of the reservoir 49a has an opening which is defined by a downwardly extending nipple 51 having a smaller-diameter extension 53 which is received in an upwardly extending socket 54 of the pump body 2a. The socket 54 receives a sealing element 55 (e.g., an O-ring) which surrounds the extension 53. The arrangement is preferably such that the ring 55 is permanently or detachably secured to the surface surrounding the socket 54 and allows for convenient insertion or lifting of the nipple 51. If the reservoir 49a forms an integral part of the housing section 49 (see FIG. 1), the ring 55 can be reached by separating the pump body 2a from supporting brackets 80 shown in FIGS. 1 and 8. Alternatively, the entire housing section 49 may be detachably mounted on the base 52 and the brackets 80 may be secured to the base so that the receptacle 49a and the section 49 may be lifted as a unit whereby the extension 53 of the nipple 51 is withdrawn from the sealing ring 55. The socket 54 may receive two or more sealing rings, depending on the length of the extension 53. Also, the sealing ring or rings can be secured to the extension 53 so that they share the movements of the nipple 51 with respect to the pump body 2a or vice versa.

In the absence of any means for preventing return flow of liquid into the reservoir 49a when the piston 15 performs a compression stroke to expel liquid from the chamber 2b, jets or streams of liquid would be likely to flow from the passage 21 into the reservoir 49a, especially when the supply of liquid in the reservoir is nearly exhausted. It has been found that such return flow of liquid is likely to occur in spite of the relatively short stroke of the valve element 30 in the inlet valve 28.

In accordance with a further feature of the invention, the appliance comprises a substantially mushroom-shaped baffle 56 having a stem or shank 56a which is inserted into the nipple 51 and a head which overlies the upper end of the axial bore of the nipple. The shank 56a has axially parallel ribs 57 which are located immediately below the head and rest on the upper side of the bottom wall 50 of the reservoir 49a. Liquid can leave the reservoir 49a by flowing through the channels or gaps between the ribs 57 and into the annular clearance between the shank 56a and the internal surface of the nipple 51.

The improved appliance exhibits a number of important advantages. Thus, the moving parts produce a surprisingly small amount of noise and the wear on such parts is negligible. Also, the energy requirements of the prime mover are small in spite of the fact that the appliance produces pronounced spurts of liquid which are beneficial to the gums and can perform a highly satisfactory cleaning action. The likelihood of malfunction is reduced because the motion transmitting means between the armature 14 and the piston 15 does not consist of or comprise crank means and also because the elements of the valves 28, 29 (as well as the element 20 of the shutoff valve) need not be biased by springs or analogous resilient elements which are likely to age and to necessitate replacement after relatively short periods of use. Moreover, the omission of crank means and valve springs contributes to simplicity and lower cost of the appliance. A frequency in the range of 50 cycles per second has been found to be highly satisfactory for massaging of gums as well as for expulsion of remnants of food or other contaminants from the spaces between teeth, behind or around bridges and crowns as well as from the spaces within and around braces. A three-pole electromechanical oscillator has been found to constitute a very satisfactory and simple prime mover for the piston of the pump 2. Such prime mover furnishes requisite power in spite of small energy requirements.

It will be readily appreciated that the improved appliance is susceptible of many further modifications without departing from the spirit of the invention. For example, the controls may include a separate starter switch, not shown, i.e., the knob 8 can be used solely as a means for changing the amplitude of the armature 14. Also, the configuration and/or dimensions of the reservoir 49a may be changed, the shutoff valve including the element 20 can be omitted or replaced by a solenoid-operated valve whose spring causes the valve element to close as soon as the user opens the circuit of the prime mover 7 or an analogous prime mover. The appliance may utilize a prime mover with a rotary output element and one or more valves whose valve elements need not be biased by springs, or vice versa. Still further, the prime mover 7 may be modified in a number of ways, for example, by reducing the number of poles to two and/or by using springs which pull the armature to its neutral position. The heating element 47 can be replaced with a heating element which surrounds a portion of the passage 21 or which is installed in the reservoir 49a.

The mode of operation of the prime mover 7 is disclosed in detail, for example, in the German Pat. No. 863,609 to Hagebeuker.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

What is claimed is:

1. In an oral hygiene appliance, a combination comprising a liquid reservoir; a nozzle; a pump having means for drawing liquid from said reservoir and for delivering spurts of liquid to said nozzle; prime mover means for driving said pump, said prime mover means comprising a multi-pole electromechanical oscillator including an oscillatory armature and means for connecting said poles to a source of alternating current; means for regulating the amplitude of oscillations of said armature; and shutoff valve means installed between said reservoir and said pump and having a valve element movable between open and closed positions, said regulating means comprising a device which is movable to and from a predetermined position in which said source is disconnected from said poles and means for moving said valve element to said closed position in response to movement of said device to said predetermined position.

2. A combination as defined in claim 1, wherein said device comprises a rotary member.

3. A combination as defined in claim 2, wherein said valve means further comprises a seat which is engaged by said valve element when the latter assumes said closed position, said valve element being reciprocable between said open and closed positions and said means for moving said valve element comprising a first threaded member which is movable with said valve element and a second threaded member in mesh with said first threaded member, one of said threaded members being rotatable by said rotary member to thereby effect the movement of said valve element to said closed position in response to rotation of said rotary member to said predetermined position.

4. A combination as defined in claim 1, wherein said prime mover means further comprises a pivot for said armature, said armature having a first arm adjacent to said poles and a second arm, said pump further comprising a body and said liquid drawing means constituting a piston which is reciprocable in said body, and further comprising means for articulately connecting said second arm of said armature to said piston.

5. A combination as defined in claim 4, wherein the length of said first arm is a multiple of the length of said second arm between said pivot and said connecting means.

6. A combination as defined in claim 5, wherein the length of said first arm is approximately 4½ times the length of said second arm.

7. A combination as defined in claim 1, wherein said pump further comprises a body and said liquid drawing means comprises a piston which is reciprocable in said body and receives motion from said prime mover means, and further comprising an inlet valve interposed between said reservoir and said pump and being open whenever said piston performs a first stroke to draw liquid from said reservoir and an outlet valve interposed between said pump and said nozzle and being open whenever said piston performs a second stroke to deliver a spurt of liquid to said nozzle.

8. A combination as defined in claim 7, wherein each of said valves comprises a valve element which is movable between open and closed positions, the distance between the open and closed positions of the valve element of said inlet valve being less than the distance between the open and closed positions of the valve element of said outlet valve.

9. A combination as defined in claim 7, wherein each first stroke of said piston is a suction stroke and each second stroke of said piston is a compression stroke, each of said valves comprising a valve element which is movable between open and closed positions and at least one of said last mentioned valve elements being moved by the conveyed liquid to one of said positions whenever said piston performs a first stroke and to the other of said positions whenever said piston performs a second stroke.

10. A combination as defined in claim 9, wherein each of said valves further comprises a seat for the respective valve element and at least said one valve element has a rounded end portion which bears against the respective seat in the closed position of said one valve element, said end portion facing counter to the direction of liquid flow through the respective valve.

11. A combination as defined in claim 9, wherein each of said valves further comprises a seat for the respective valve element and at least said one valve element has a conical end portion which bears against the respective seat in the closed position of said one valve element, said end portion of said one valve element facing counter to the direction of liquid flow through the respective valve.

12. A combination as defined in claim 7, wherein each of said valves comprises a valve element which is movable between open and closed positions, at least one of said last mentioned valve elements being hollow.

13. A combination as defined in claim 7, wherein each of said valves further comprises a housing and a valve element movable in said housing between open and closed positions, at least one of said last mentioned valve elements having external fins which are slidable in the respective housing and define channels for the flow of liquid through the respective valve in the open position of said one valve element.

14. A combination as defined in claim 7, wherein each of said valves comprises a valve element which is movable betwen open and closed positions, the valve element of said inlet valve being movable along a substantially horizontal path between said open and closed positions thereof.

15. A combination as defined in claim 1, wherein said pump further comprises a body having a bore and said liquid drawing means comprises a piston which is reciprocable in said bore and includes a first portion which is received in said bore with at least some clearance and a deformable second portion which bears against the surface surrounding said bore.

16. A combination as defined in claim 15, further comprising means for urging said second portion of said piston against said surface.

17. A combination as defined in claim 16, wherein said piston has an annular groove which is surrounded by said second portion thereof and said urging means comprises an elastic ring-shaped spreading element in said groove.

18. A combination as defined in claim 17, wherein said body defines a chamber into which said piston draws liquid from said reservoir while moving in a first direction and from which said piston expels liquid into said nozzle while moving in a second direction, said piston further having an end wall which is adjacent to said chamber and said second portion thereof being adjacent to said end wall, said groove being provided in said end wall.

19. A combination as defined in claim 1, wherein said pump further comprises a body and said liquid drawing means comprises a piston which is reciprocable in said body, said piston having an outer diameter in the range of 6–20 millimeters.

20. A combination as defined in claim 19, wherein the outer diameter of said piston is approximately twelve millimeters.

21. A combination as defined in claim 1, further comprising conduit means connecting said pump with said nozzle and means for heating the liquid in said conduit means, said regulating means further comprising means for activating or deactivating said heating means.

22. A combination as defined in claim 1, wherein said pump comprises a body and said liquid withdrawing means comprises a pumping element movably installed in said body, said body having a passage which supplies liquid from said reservoir into the range of said pumping element and said reservoir having a downwardly extending nipple defining an outlet for liquid, said body having a socket for said nipple and further comprising sealing means provided in said socket and surrounding said nipple.

23. A combination as defined in claim 22, wherein said nipple has an extension which is received in said socket and said sealing means comprises at least one ring surrounding said extension.

24. A combination as defined in claim 1, wherein said pump further comprises a body and said liquid drawing means comprises a pumping element movably mounted in said body, said body having a passage for admission of liquid into the range of said element and said reservoir having an outlet located above and communicating with said passage, and further comprising a baffle provided in said outlet to prevent streams of liquid from rising above the level of liquid in said reservoir when said element delivers spurts of liquid to said nozzle.

25. A combination as defined in claim 24, wherein said pumping element is a piston which performs alternating suction and compression strokes to draw liquid from said outlet during each suction stroke and to expel liquid into said nozzle during each compression stroke.

26. In an oral hygiene appliance, a combination comprising a liquid reservoir; a nozzle; a pump having means for drawing liquid from said reservoir and for delivering spurts of liquid to said nozzle; prime mover means for driving said pump, said prime mover means comprising a multi-pole electromechanical oscillator, said pump further comprising a body and said liquid drawing means comprising a piston which is reciprocable in said body and receives motion from said prime mover means; an inlet valve interposed between said reservoir and said pump and being open whenever said piston performs a first stroke to draw liquid from said reservoir; and an outlet valve interposed between said pump and said nozzle and being open whenever said piston performs a second stroke to deliver a spurt of liquid to said nozzle, said outlet valve having a valve element which is movable between open and closed positions and the distance between said open and closed positions being such that said outlet valve remains open during the initial stage of each first stroke of said piston.

27. The combination of claim 26, wherein said oscillator is a three-pole oscillator including an oscillatory armature and means for connecting said poles to a source of alternating current.

28. The combination of claim 27, further comprising means for regulating the amplitude of oscillations of said armature.

29. A combination as defined in claim 28, wherein said regulating means comprises a device which is operable to change the amplitude of oscillations of said armature in stepwise fashion.

30. A combination as defined in claim 28, wherein said regulating means comprises a device for selecting for said armature any one of an infinite number of amplitudes.

31. A combination as defined in claim 30, wherein said device comprises variable resistor means.

32. A combination as defined in claim 26, wherein said first strokes are suction strokes and said piston draws a relatively small quantity of liquid into said body by way of said outlet valve during said initial stage of each of said first strokes.

33. A combination as defined in claim 27, wherein said source is to a standard source of alternating current, and further comprising means for transmitting motion from said armature to said pumping element so that the latter reciprocates at the frequency of oscillation of said armature.

34. In an oral hygiene appliance, a combination comprising a liquid reservoir; a nozzle; a pump having means for drawing liquid from said reservoir and for delivering spurts of liquid to said nozzle; prime mover means for driving said pump, said prime mover means comprising a multi-pole electromechanical oscillator, said pump further comprising a body and said liquid drawing means comprising a piston which is reciprocable in said body and receives motion from said prime mover means; an inlet valve interposed between said reservoir and said pump and being open whenever said piston performs a first stroke to draw liquid from said reservoir; and an outlet valve interposed between said pump and said nozzle and being open whenever said piston performs a second stroke to deliver a spurt of liquid to said nozzle, each of said valves comprising a valve element which is reciprocable between open and closed positions and at least one of said valve elements having a blind bore with an open end at the downstream side of the respective valve element, as considered in the direction of liquid flow through the respective valve.

35. In an oral hygiene appliance, a combination comprising a liquid reservoir; a nozzle; a pump having menas for drawing liquid from said reservoir and for delivering spurts of liquid to said nozzle; prime mover means for driving said pump, said prime mover means comprising a multi-pole electromechanical oscillator including an oscillatory armature and a pivot for said armature, said armature having a first arm which is adjacent to the poles of said prime mover means and a second arm, said pump further having a body and said liquid drawing means comprising a piston which is reciprocable in said body; and means for transmitting motion from said second arm of said armature to said piston, said second arm being adjacent to one side of said piston and said motion transmitting means comprising a first connecting member extending diametrically of and movable axially in said piston and a second connecting member attached to said second arm and coupled to said first connecting member, said members being disposed at right angles to each other.

36. A combination as defined in claim 35, wherein said second connecting member is substantially normal to the second arm of said armature.

37. A combination as defined in claim 35, wherein said connecting members are pins, said second connecting member being rotatable relative to said second arm and/or said first connecting member.

* * * * *

UNITED STATES PATENT AND TRADEMARK OFFICE
CERTIFICATE OF CORRECTION

PATENT NO. : 4,141,352
DATED : February 27, 1979
INVENTOR(S) : Albert Ebner and Kurt Bauerle It is certified that error appears in the above-identified patent and that said Letters Patent are hereby corrected as shown below:

Col. 3, line 36, "of shaft 26" should read --or shaft 26--;
Col. 5, line 46, "diameterically" should read --diametrically--;
Col. 9, line 55, "compession" should read --compression--;
Col. 14, line 43, "menas" should read --means--; and
Col. 14, line 15, "is to a standard" should read --is a standard--.

Signed and Sealed this

Sixth Day of November 1979

[SEAL]

Attest:

RUTH C. MASON
Attesting Officer

LUTRELLE F. PARKER
Acting Commissioner of Patents and Trademarks